US00PP30087P3

(12) United States Plant Patent
Caton

(10) Patent No.: US PP30,087 P3
(45) Date of Patent: Jan. 15, 2019

(54) ***VACCINIUM* PLANT NAMED 'VACBRI 1'**

(50) Latin Name: *Vaccinium corymbosum*
Varietal Denomination: VacBri 1

(71) Applicant: Lynne Caton, Olympia, WA (US)

(72) Inventor: Lynne Caton, Olympia, WA (US)

(73) Assignee: Gurjit Sidhu, Mission (CA)

( * ) Notice: Subject to any disclaimer, the term of this patent is extended or adjusted under 35 U.S.C. 154(b) by 0 days.

(21) Appl. No.: 15/530,939

(22) Filed: Mar. 27, 2017

(65) Prior Publication Data

US 2017/0311500 P1 Oct. 26, 2017

(30) Foreign Application Priority Data

Apr. 26, 2016 (CA) ..... PBR 16-8904

(51) Int. Cl.
*A01H 5/08* (2018.01)

(52) U.S. Cl.
USPC ..... Plt./157
CPC ..... *A01H 5/08* (2013.01)

(58) Field of Classification Search
USPC ..... Plt./157
See application file for complete search history.

*Primary Examiner* — Susan McCormick Ewoldt
(74) *Attorney, Agent, or Firm* — Penny J. Aguirre

(57) ABSTRACT

A new cultivar of *Vaccinium*, 'VacBri1', that is characterized by its young foliage that emerges dark purple in color in spring, its foliage color that becomes mottled dark purple and green in color during the growing season and its blue berries that are produced mid-season.

2 Drawing Sheets

Botanical classification: *Vaccinium corymbosum.*
Cultivar designation: 'VacBri1'.

BACKGROUND OF THE INVENTION

The present invention relates to a new and distinct cultivar of *Vaccinium corymbosum*, and will be referred to hereafter by its cultivar name, 'VacBri1'. 'VacBri1' is a new cultivar of northern highbush blueberry grown for use as a fruit bearing landscape shrub.

The new cultivar was discovered by the Inventor in summer of 2008 as a naturally occurring branch mutation of *Vaccinium corymbosum* 'Toro' (not patented) that was growing in a container at a nursery in Elma, Wash.

Asexual propagation of the new cultivar was first accomplished under the direction of the Inventor by tissue culture using meristematic tissue in Elma, Wash. in September of 2009. Asexual propagation by tissue culture has determined that the characteristics of this cultivar are stable and are reproduced true to type in successive generations.

SUMMARY OF THE INVENTION

The following traits have been repeatedly observed and represent the characteristics of the new cultivar, which in combination distinguish 'VacBri1' as a new and distinct cultivar of *Vaccinium.*

1. 'VacBri1' exhibits young foliage that emerges dark purple in color in spring.
2. 'VacBri1' exhibits foliage color that becomes mottled dark purple and green in color during the growing season.
3. 'VacBri1' exhibits blue berries that are produced mid-season.

'Toro', the parent plant of 'VacBri1', is similar to 'VacBri1' in hardiness, growth habit, flowering and fruiting season. 'Toro', differs to 'VacBri1' in having foliage that are only green in color. 'VacBri1' can also be compared to the cultivar 'Bluecrop' (not patented). 'Bluecrop' is similar to 'VacBri1' in in hardiness, growth habit, flowering and fruiting season. 'Bluecrop' differs from 'VacBri1' in having leaves that are only green in color.

BRIEF DESCRIPTION OF THE DRAWINGS

The accompanying colored photographs illustrate the overall appearance and distinct characteristics of the new *Vaccinium*. The photographs in FIG. 1 and FIG. 2 were taken of a 3 year-old plant as grown outdoors in Elma, Wash. in a 2-gallon container. The photographs in FIG. 3 and FIG. 4 were taken of a 2-year-old plant as grown in a one-gallon container in St. Thomas, Ontario in a poly greenhouse.

The photograph in FIG. 1 provides a side view of 'VacBri1' in fruit.

Figure 1:
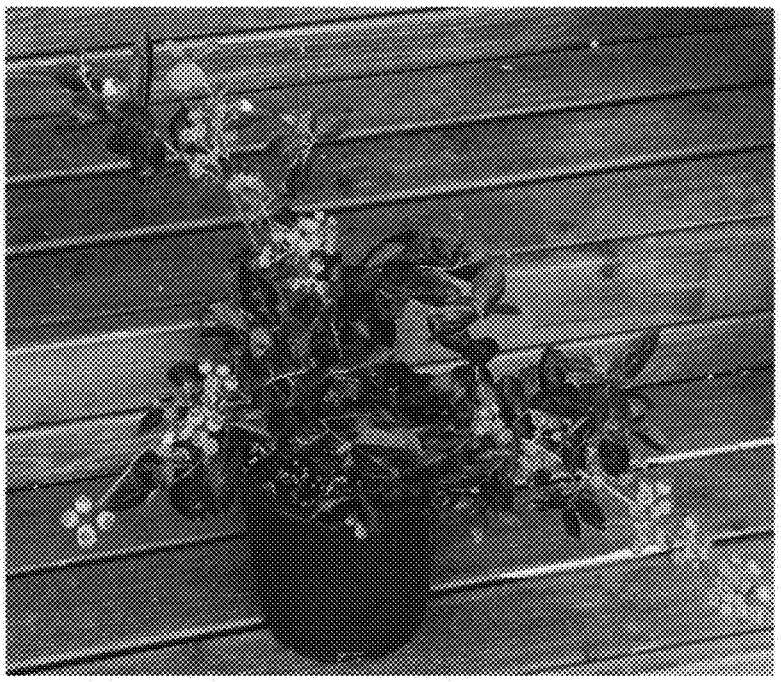
Figure 2:
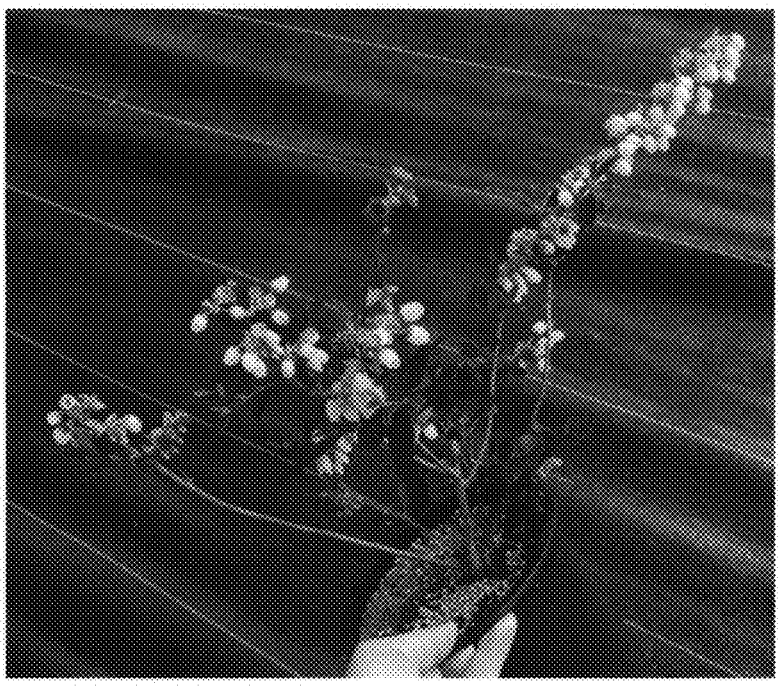

The photograph in FIG. 2 provides a view of 'VacBri1' in bloom.

Figure 3:
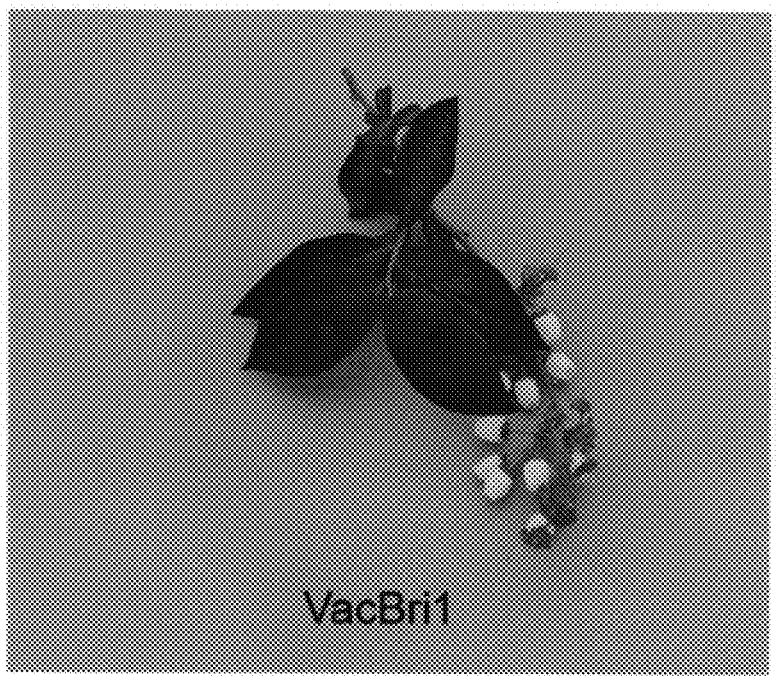

The photograph in FIG. 3 provides a close-up view of the foliage and flowers of 'VacBri1'.

Figure 4:
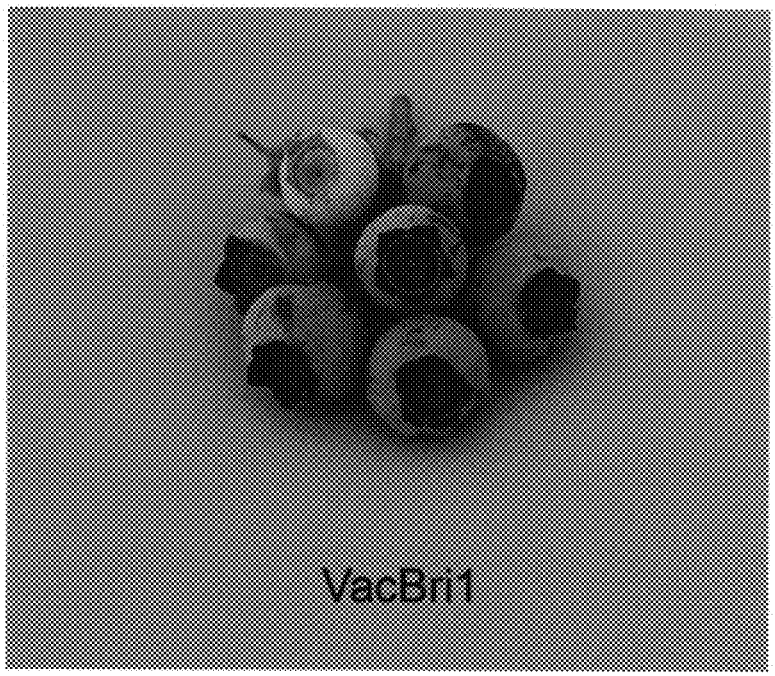

The photograph in FIG. 4 provides a close-up view of the fruit of 'VacBri1'.

The colors in the photographs may differ slightly from the color values cited in the detailed botanical description, which accurately describe the colors of the new *Vaccinium.*

DETAILED BOTANICAL DESCRIPTION OF THE PLANT

The following is a detailed description of 2-year-old plant as grown in one-gallon containers in St. Thomas, Ontario, Canada in a poly greenhouse. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Blooming period.*—Spring, followed by edible berries in the summer in St. Thomas, Ontario, Canada.

*Plant type.*—Deciduous shrub fruit bearing shrub.

*Plant habit.*—Semi-erect.

*Height and spread.*—Mid size plant stature; reaching about 1.2 m in height and 1.2 m in width as a mature plant.

*Hardiness.*—Hardy in at least U.S.D.A. Zones 4 to 8.

*Disease resistance.*—No susceptibility or resistance to diseases has been observed.

*Root description.*—Fibrous.

*Growth rate.*—Moderate to vigorous.

*Propagation.*—Tissue culture.

*Root development.*—A tissue culture plantlet will root in a small plug cell in 3 months, the transplanted rooted plug will finish in a liner in 5 to 6 months.

Stem description:

*Mature canes.*—Closest to N199C in color, an average of 75.7 cm in length and 5.7 mm in width on a 2 year old plant, bark surface ranges from smooth to rough.

*Dormant stems (previous years growth).*—Closest to 144B in color, average of 63.2 cm in length and 4.3 mm diameter at the base, surface is glabrous to sparsely pubescent, internode length; an average of 12 cm, ranging from 9.1 cm to 14.0 cm.

*New growth.*—144B in color with overlay of anthocyanin coloration of 178A on the sunny side.

*Branching.*—Medium.

*Suckering.*—Medium.

Foliage description:

*Leaf shape.*—Elliptic.

*Leaf division.*—Simple.

*Leaf base.*—Cuneate to rounded.

*Leaf apex.*—Acute.

*Leaf venation.*—Pinnate, color on upper and lower surfaces matches leaf coloration.

*Leaf margins.*—Entire.

*Leaf attachment.*—Petiolate.

*Leaf arrangement.*—Alternate.

*Leaf orientation.*—Held slightly upward.

*Leaf surface.*—Upper and lower surface glabrous, medium glossiness, with occasional sparse pubescence on the leaf margin and mid vein on upper surface.

*Leaf color.*—Newly expanded leaves upper surface; N186C, newly expanded leaves lower surface; 191B with overlay of anthocyanin coloration of 187C, mature leaves upper surface; 187A mottled with 146A changing to mostly 146A by late summer, mature leaves lower surface; 147B to 147C, fall color upper surface; redder than 200A, fall color lower surface; 147C mottled with 187B to 185B.

*Leaf size.*—Average of 6.3 cm in length (ranging 5.9 to 7.2 cm), an average of 3.8 cm in width, ranging from 3.5 to 4.4 cm in width.

*Leaf blade length/width ratio.*—1.7.

*Petioles.*—Round in shape, an average of 4 mm in length and 1.4 mm in width, 145C in color, glabrous surface.

*Stipules.*—None observed.

Inflorescence description:

*Bloom season.*—Buds burst mid April in St. Thomas, Ontario, Canada, flowering begins in May in St. Thomas, Ontario, Canada as grown in a greenhouse, bud burst and bloom time are highly variable depending on season.

*Inflorescence.*—Cluster, average of 3.1 cm in length 3.0 cm in width.

*Lastingness of inflorescence.*—Average of 28 days but highly dependent on temperatures.

*Number of flowers.*—Average of 9 per inflorescence, range of 7 to 12.

*Flower fragrance.*—None to slight.

*Flower size.*—Average of 8.4 mm in length and 7.8 mm in width.

*Flower buds.*—9 per inflorescence, ovate in shape, 8 mm in length and 4 mm in width.

*Corolla.*—Urceolate in shape, comprised of 5 fused petals with tip free and curled under, average of 8.4 mm in length and 7.8 mm in width, aperture is an average of 3.8 mm in diameter, color NN155A on outer and inner surface with outer surface sometimes tinged with 51A with sun exposure, glabrous texture on both surfaces.

*Calyx.*—Campanulate, comprised of 5 fused sepals with lobes free at apex, average of 8 mm in diameter, free sepal lobes an average of about 2.3 mm in length and 2.7 mm in width at anthesis, color 144A to 144B on outer and inner surface and tinged at the distil end with 178A with sun exposure, surface glabrous.

*Pedicels.*—Round, average of 6.2 mm in length and 1.1 mm in width, closest to 143D in color and slightly suffused with 178A, surface is glabrous.

*Peduncles.*—Round, an average of 7 mm in length and 1.6 mm in width, closest to 144C in color, surface is glabrous.

Reproductive organs:

*Androecium.*—10 stamens, stamens are 5 mm in length, anthers are 164A in color and 2.2 mm in length, filaments are 3 mm in length and 145C in color, pollen is moderate in abundance and 4D in color.

*Gynoecium.*—1 pistil, style is cone-shaped, an average of 9.1 mm in length (approximately equal to tip of corolla) and 145B in color, ovary 144A in color.

Fruit description:

*Type.*—Berry.

*Number.*—4 to 10 per cluster.

*Cluster tightness.*—Medium.

*Skin color.*—Unripe; 138D (with bloom), and 144B (without bloom), ripening (mature fruit); closest to 98C (with bloom), closest to 202A (without bloom).

*Date of fruit ripening.*—Medium season for 50% ripe.

*Picking dates.*—First pick early July, last pick mid July in St. Thomas, Ontario, Canada.

*Skin surface.*—Medium to high level of glaucous coating (bloom).

*Shape.*—Larger berries transversely elliptic, smaller berries globose.

*Flesh color.*—144D.

*Flesh texture.*—Fleshy.

*Calyx.*—Campanulate, comprised of 5 fused sepals with lobes free at apex, color 144A and suffused with N187A on outer and inner surface, glaucous surface, free lobes; average of 1.8 mm in length and 3.7 mm in width, triangular in shape, diameter of aperature; average of 5.8 mm.

*Scar size*.—Average of 1.9 mm in diameter.

*Flavor*.—Sweet taste with moderate aroma.

*Firmness*.—Moderately firm.

*Weight*.—1.34 g mean (100 berries sampled).

*Diameter*.—Average of 1.41 cm in diameter

*Brix*.—12 degrees.

*Productivity*.—Similar to the parent plant, 'Toro', 15 to 18 lbs. per mature bush.

*Storage life*.—Has not been established, fruit is grown by home gardeners.

*Seeds*.—Abundant, N167A in color, average of 1.3 mm in length and 0.7 mm in width.

*Self incompatibility*.—Has not been established, fruit is grown by home gardeners.

*Market use*.—Fresh fruit for home gardeners.

It is claimed:

1. A new and distinct cultivar of *Vaccinium* plant named 'VacBri1' as herein illustrated and described.

* * * * *